(12) United States Patent
Ishihara et al.

(10) Patent No.: US 8,680,322 B2
(45) Date of Patent: Mar. 25, 2014

(54) METHOD FOR PRODUCING ALPHA-ACYLOXYCARBONYL COMPOUND AND NOVEL ALPHA-ACYLOXYCARBONYL COMPOUND

(75) Inventors: Kazuaki Ishihara, Nagoya (JP); Muhammet Uyanik, Nagoya (JP)

(73) Assignees: National University Corporation Nagoya University, Nagoya-shi (JP); Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 13/581,734

(22) PCT Filed: Mar. 4, 2011

(86) PCT No.: PCT/JP2011/055043
§ 371 (c)(1),
(2), (4) Date: Aug. 29, 2012

(87) PCT Pub. No.: WO2011/108696
PCT Pub. Date: Sep. 9, 2011

(65) Prior Publication Data
US 2012/0323014 A1    Dec. 20, 2012

(30) Foreign Application Priority Data
Mar. 5, 2010    (JP) .................................. 2010-049003

(51) Int. Cl.
*C07C 249/00*    (2006.01)

(52) U.S. Cl.
USPC ....................................................... 560/336

(58) Field of Classification Search
USPC ....................................................... 560/336
See application file for complete search history.

(56) References Cited

U.S. PATENT DOCUMENTS

| | | | |
|---|---|---|---|
| 4,922,004 A | 5/1990 | Köhler et al. | |
| 2007/0059639 A1 | 3/2007 | Kanda et al. | |

FOREIGN PATENT DOCUMENTS

| | | | |
|---|---|---|---|
| JP | 62-81345 A | 4/1987 | |
| JP | 2005-99327 A | 4/2005 | |
| JP | 2007-304545 A | 11/2007 | |
| JP | 2009-144071 A | 7/2009 | |
| KR | 10-2011-0029576 A | 3/2011 | |

OTHER PUBLICATIONS

Ochiai et al. J.Am.Chem.Soc., 2005, 127, 12244-12245.*
Uyanik et al. Angewandte Chemie (International ed. in English) (2011), 50(23), 5331-4.*
International Search Report issued Jun. 7, 2011 in PCT/JP2011/055043.
Masahito Ochiai, et al., "Iodobenzene-Catalyzed α-Acetoxylation of Ketones. In Situ Generation of Hypervalent (Diacyloxyiodo)benzenes Using m-Chloroperbenzoic Acid", Journal of the American Chemical Society, 127(35), 2005, pp. 12244-12245.
Toshifumi Dohi, et al., "Hypervalent iodine reagents as a new entrance to organocatalysts", Chem. Commun 2009, pp. 2073-2085.
Jun Yu, et al., "Various α-Oxygen Functionalizations of β-Dicarbonyl Compounds Mediated by the Hypervalent Iodine(III) Reagent p-Iodotoluene Difluoride with Different Oxygen-Containing Nucleophiles", Advanced Synthesis & Catalysis, 352, 2010, pp. 531-546.
Takeshi Yasui, et al., "Chiral Hypervalent Iodine-Catalyzed Oxidative Oxylactonization of Ketocarboxylic Acids with Hydrogen Peroxide", CSJ: The Chemical Society of Japan Koen Yokoshu, vol. 89th, No. 2, Mar. 13, 2009, p. 1170 plus cover pages.
Daisuke Suzuki, et al., "Cho Genshika Yoso Kagobutsu o Shokubai ni Mochiiru Carbonyl Kagobutsu to Carboxylic Acid no Sankateki Bunshikan Coupling Hanno", CSJ: The Chemical Society of Japan Koen Yokoshu, vol. 90th, No. 4, Mar. 12, 2010, pp. 1307 plus cover pages.
Youngjoon Lee, et al., "Investigation of cyclopolymerization for ArF positive photoresist", Proceedings of the SPIE—The International Society for Optical Engineering, vol. 5039, part 2, Feb. 24-26, 2003, pp. 682-688 plus cover page.
Ayhan S. Demir, et al., "Potassium permanganate/carboxylic acid/organic solvent: a powerful reagent for enone oxidation and aryl coupling reactions", Tetrahedron, 64(27), 2008, pp. 6196-6201.
Chih-Ho Tai, et al., "Studies on a Novel Safety-Catch Linker Cleaved by Pummerer Rearrangement", Organic Letters, vol. 6, No. 17, 2004, pp. 2905-2908.

* cited by examiner

*Primary Examiner* — Nizal Chandrakumar
(74) *Attorney, Agent, or Firm* — Oblon, Spivak, McClelland, Maier & Neustadt, L.L.P.

(57) ABSTRACT

A method for producing an α-acyloxycarbonyl compound of the present invention includes performing an intermolecular reaction between a carboxylic acid and a carbonyl compound selected from the group consisting of ketones, aldehydes, and esters, which have a hydrogen atom at the α-position, using a hydroperoxide as an oxidizer and an iodide salt as a catalyst precursor, thereby introducing an acyloxy group derived from the carboxylic acid into the α-position of the carbonyl compound.

20 Claims, No Drawings

METHOD FOR PRODUCING ALPHA-ACYLOXYCARBONYL COMPOUND AND NOVEL ALPHA-ACYLOXYCARBONYL COMPOUND

TECHNICAL FIELD

The present invention relates to a method for producing an α-acyloxycarbonyl compound and to a novel α-acyloxycarbonyl compound.

BACKGROUND ART

α-Oxycarbonyl compounds are useful skeletons for many natural products and medicinal products. A conventional method for synthesizing α-acyloxycarbonyl compounds uses a stoichiometric amount of a highly toxic heavy metal oxidizer (Pb, Mn, Ti). Also, a synthesis method using a hypervalent iodine compound in place of a heavy metal oxidizer has recently been reported. Recent examples include intermolecular coupling reactions between ketones and acetic acid developed by Ochiai et al. (Non-Patent Document 1). Specifically, compounds are produced by acyloxylation at the α-positions of ketones in an acetic acid solvent in the presence of a stoichiometric amount of Lewis acid using a hypervalent iodine compound in-situ prepared from a catalytic amount of iodobenzene and meta-chloroperbenzoic acid (mCPBA).

CITATION LIST

Non-Patent Document

Non-Patent Document 1: Journal of American Chemical Society (J. Am. Chem. Soc.), 2005, vol. 127, p. 12244

DISCLOSURE OF INVENTION

However, it is essential for the above-described method to use 3 equivalents or more of Lewis acid ($BF_3 \cdot Et_2O$) relative to a reaction substrate. In addition, acetic acid serving as the reaction substrate is used in a solvent amount, i.e., a large excess. Further, the applicability of the reaction substrate is not so wide.

The present invention has been achieved for resolving the above-described problems, and a main object of the present invention is to provide a method for producing an α-acyloxycarbonyl compound without the need to use a Lewis acid and a large excess of carboxylic acid serving as a reaction substrate, the reaction substrate having wide applicability.

In order to achieve the above object, the inventors of the present invention attempted an intermolecular α-acyloxylation reaction between a carboxylic acid and a carbonyl compound selected from the group consisting of ketones, aldehydes, and esters, which have a hydrogen atom at the α-position, using an iodide salt and hydroperoxide. As a result, it was found that an intended α-acyloxycarbonyl compound can be produced in high yield, leading to the achievement of the present invention.

That is, a method for producing an α-acyloxycarbonyl compound of the present invention includes performing an intermolecular reaction between a carboxylic acid and a carbonyl compound selected from the group consisting of ketones, aldehydes, and esters, which have a hydrogen atom at the α-position, using hydroperoxide as an oxidizer and an iodide salt as a catalyst precursor, thereby introducing an acyloxy group derived from the carboxylic acid into the α-position of the carbonyl compound.

According to the method for producing an α-acyloxycarbonyl compound of the present invention, an α-acyloxycarbonyl compound can be produced without the need to use a Lewis acid and a large excess of carboxylic acid as a reaction substrate. In addition, a ketone, aldehyde, or ester can be used as the carbonyl compound in which the acyloxy group derived from the carboxylic acid is introduced, thereby extending the applicability of the reaction substrate. In the method for producing an α-acyloxycarbonyl compound, the reaction is considered to proceed according to a formula described below. In the formula, for convenience sake, propiophenone is shown as an example of the carbonyl compound, and benzoic acid is shown as an example of the carboxylic acid. First, a reaction between the iodide salt ($Z^+I^-$: wherein $Z^+$ is a counter cation) and hydroperoxide (ROOH: R is hydrogen or alkyl) proceeds to produce a hypervalent iodine compound and a reduced compound (ROH) of hydroperoxide. Next, an intermolecular reaction between the carboxyl compound and the carboxylic acid proceeds in the presence of the produced hypervalent iodine compound functioning as a catalyst, producing an α-acyloxycarbonyl compound. At the same time, the hypervalent iodine compound is returned to the iodide salt (catalyst precursor).

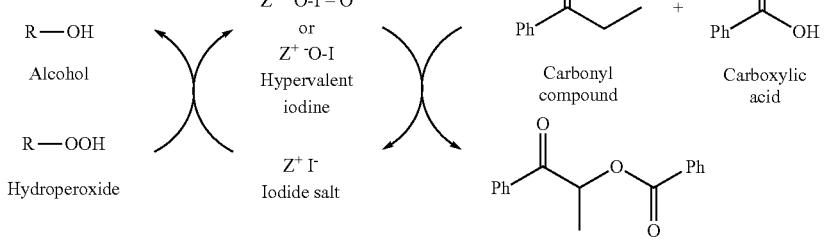

BEST MODE FOR CARRYING OUT THE INVENTION

A method for producing an α-acyloxycarbonyl compound of the present invention includes performing an intermolecular reaction between a carboxylic acid and a carbonyl compound selected from the group consisting of ketones, aldehydes, and esters, which have a hydrogen atom at the α-position, using hydroperoxide as an oxidizer and an iodide salt as a catalyst precursor, thereby introducing an acyloxy group derived from the carboxylic acid into the α-position of the carbonyl compound.

In the method for producing an α-acyloxycarbonyl compound of the present invention, a water solution of hydrogen peroxide and organic hydroperoxide can be used as the hydroperoxide. The organic hydroperoxide is preferred. Examples of the organic hydroperoxide include tert-butyl hydroperoxide and cumene hydroperoxide. Tert-butyl hydroperoxide is preferred. In addition, the water solution of hydrogen peroxide is inexpensive and thus may be advantageous from the economical viewpoint even if the yield of the α-acyloxycarbonyl compound is lower than that of the organic hydroperoxide. The hydroperoxide is preferably used at 1 to 5 equivalents, more preferably 1.1 to 2.5 equivalents, relative to, of the carboxylic acid and the carbonyl compound, one having a smaller number of moles. An excessively small amount of use is undesired because the reaction may not be completed in view of the reaction mechanism, while an excessively large amount of use is undesired from the economical viewpoint because the yield is not significantly improved thereby. A preferred usage form of the hydroperoxide is a form diluted with a solvent. In this case, either an organic solvent (for example, a hydrocarbon solvent such as decane) or water may be used as the solvent.

In the method for producing an α-acyloxycarbonyl compound of the present invention, an ammonium iodide, a phosphonium iodide, an alkali metal iodide, or the like can be used as the iodide salt. Examples of the ammonium iodide include tetraalkylammonium iodides (in tetraalkyl, all four alkyl groups may be the same, two or three alkyl groups may be the same, or all alkyl groups may be different), tetraarylammonium iodides (in tetraaryl, all four aryl groups may be the same, two or three aryl groups may be the same, or all aryl groups may be different), tetraarylalkylammonium iodides (in tetraarylalkyl, all four arylalkyl groups may be the same, two or three arylalkyl groups may be the same, or all arylalkyl groups may be different), ammonium iodides in which alkyl and aryl are mixed, alkyl and arylalkyl are mixed, or aryl and arylalkyl are mixed, and the like. Examples of such ammonium iodides include tetramethylammonium iodide, tetraethylammonium iodide, tetrapropylammonium iodide, tetrabutylammonium iodide, tetrapentylammonium iodide, tetrahexylammonium iodide, tetraheptylammonium iodide, tetra-n-octylammonium iodide, tetraoctadecylammonium iodide, ethyltrimethylammonium iodide, ethyltripropylammonium iodide, trimethylphenylammonium iodide, triethylphenylammonium iodide, (1,2-diphenylpropyl)trimethylammonium iodide, trimethyl-(1-phenylethyl)ammonium iodide, benzyltriethylammonium iodide, and the like. Among these, ammonium iodides having four alkyl groups each having 1 to 18 carbon atoms are preferred. The phosphonium iodide is similar to the ammonium iodide. Examples of the phosphonium iodide include tetraphenylphosphonium iodide, methyltriphenylphosphonium iodide, tribuylmethylphosphonium iodide, and the like. Among these, tetraphenylphosphonium iodide and methyltriphenylphosphonium iodide are preferred. Examples of the alkali metal iodides include potassium iodide, sodium iodide, and the like. When such an alkali metal iodide is used in an organic solvent, a cyclic ether such as crown ether, which can take in alkali metal ions, is preferably combined for enhancing solubility. For example, potassium iodide is preferably used in combination with 18-crown-6. In addition, an iodide salt is preferably used at 1 to 50 mol %, more preferably 5 to 20 mol %, relative to, of the carboxylic acid and the carbonyl compound, one having a smaller number of moles. An excessively small amount of use is undesired because the reaction rate is decreased, and thus a long time is required until the reaction is completed, while an excessively large amount of use is undesired from the economical viewpoint because the yield is not significantly improved thereby.

In the method for producing an α-acyloxycarbonyl compound of the present invention, at least one selected from the group consisting of ether solvents, ester solvents, and nitrile solvents is preferably used as a reaction solvent. Although the carboxylic acid or the carbonyl compound used as the reaction substrate may also be used as the reaction solvent, this is undesirable for the use of an expensive reaction substrate, and thus a generally known reaction solvent is used. In this case, at least one selected from the group consisting of ether solvents, ester solvents, and nitrile solvents is preferably used, and ester solvents are more preferred. The ether solvents include diethyl ether, tetrahydrofuran, 1,4-dioxane, and the like. The ester solvents include methyl acetate, ethyl acetate, and the like. The nitrile solvents include acetonitrile, propionitrile, butyronitrile, and the like. In addition, even when the oxidizer contains water, the reaction proceeds, and thus water need not be positively removed from the reaction system.

In the method for producing an α-acyloxycarbonyl compound of the present invention, the reaction temperature may be properly set according to the reaction substrates, but is preferably 25° C. or more and more preferably 50° C. or more. The reaction temperature of less than 25° C. is undesired because the reaction rate is decreased, and thus a long time is required until the reaction is completed. The upper limit of the reaction temperature may be properly determined to, for example, 100° C. or less, so as to avoid the reaction substrates from being decomposed and side reactions from becoming dominant. Also, the reaction time may be properly set according to the reaction substrates.

In the method for producing an α-acyloxycarbonyl compound of the present invention, the carbonyl compound preferably has a methylene ($-CH_2-$) bond to carbonyl carbon, i.e., a partial structure, $-C(=O)-CH_2-$. In this case, a hydrogen atom at the α-position is a hydrogen atom of methylene. In the case of a methylene bond, the α-acyloxylation reaction of the carbonyl compound desirably easily proceeds as compared with the case of a methyl or methine bond to carbonyl carbon.

In the method for producing an α-acyloxycarbonyl compound of the present invention, the carbonyl compound and the carboxylic acid used as the reaction substrates have very wide applicability. As the carbonyl compound, any one of ketones, aldehydes, esters can be used. These include 1,3-diketones, 1,3-dialdehydes, 1,3-diesters, 1,3-ketoaldehydes, and 1,3-ketoesters. As such a carbonyl compound, one represented by $R^a-C(=O)-CH_2-R^b$ or $R^a-C(=O)-CH_2-C(=O)-R^c$ can be used. Examples of $R^a$ include a hydrogen atom, alkyl, cycloalkyl, alkenyl, cycloalkenyl, alkynyl, aryl, heterocycle, alkoxy, cycloalkoxy, aryloxy, and the like, which, excluding a hydrogen atom, may have a substituent. Examples of $R^b$ include alkyl, cycloalkyl, alkenyl, cycloalkenyl, alkynyl, aryl, heterocycle, alkoxy, cycloalkoxy, aryloxy, and the like, which may have a substituent. Examples of $R^c$ include a hydrogen atom, alkyl, cycloalkyl, alkenyl, cycloalkenyl, alkynyl, aryl, heterocycle, alkoxy, cycloalkoxy, aryloxy, and the like, which may have a substituent. In addition, $R^a$ and $R^b$ may be bonded to each other to form a hydrocarbon chain, and at least one hydrogen atom of the hydrocarbon chain may be substituted with a substituent. $R^a$ and $R^c$ may be bonded to each other to form a hydrocarbon chain, and at least one hydrogen atom of the hydrocarbon chain may be substituted with a substituent. In addition, at least one carbon atom of the hydrocarbon chain may be substituted with a heteroatom (O, S, NH, or NR wherein R is alkyl). Examples of such a carbonyl compound include tetrahydropyranone, indanone, tetralone, and derivatives thereof, and the like.

Examples of alkyl include, but are not particularly limited to, methyl, ethyl, propyl, isopropyl, n-butyl, isobutyl, sec-butyl, tert-butyl, and the like. Examples of cycloalkyl include, but are not particularly limited to, cyclopropyl, cyclopentyl, cyclohexyl, and the like. Examples of alkenyl include, but are not particularly limited to, ethenyl, propenyl, butenyl, and the like. Examples of cycloalkenyl include, but are not particularly limited to, cyclopentenyl, cyclohexenyl, and the like. Examples of alkynyl include, but are not particularly limited to, ethynyl, propynyl, butynyl, and the like. When alkyl, cycloalkyl, alkenyl, cycloalkenyl, alkynyl each have a substituent, a halogen atom, nitro, nitrile, aryl, heterocycle, alkoxycarbonyl, alkoxy, silyloxy, and the like can be used as the substituent. Examples of aryl and heterocycle are described below.

Examples of aryl include, but are not particularly limited to, phenyl and naphthyl, substitution products thereof, in which at least one hydrogen atom is substituted with a substituent, and the like. Examples of heterocycle include, but are not limited to, pyrrolyl, imidazolyl, pyrazolyl, triazolyl, tetrazolyl, pyridyl, pyrimidinyl, pyridazinyl, pyrazinyl, triazinyl, tetrazinyl, oxazolyl, isooxazolyl, thiazolyl, isothiazolyl, condensed-ring compounds thereof with benzene, naphthalene, or cycloalkane, and substitution products thereof, in which at least one hydrogen atom is substituted with a substituent, and the like. In this case, examples of the substituent include halogen atoms, nitro, nitrile, alkyl, cycloalkyl, alkenyl, cycloalkenyl, alkynyl, alkoxy, cycloalkoxy, aryl, and the like. Specific examples of alkyl, cycloalkyl, alkenyl, cycloalkenyl, aryl, and alkynyl are as described above. Examples of alkoxy and cycloalkoxy are described below.

Examples of alkoxy include, but are not particularly limited to, methoxy, ethoxy, propoxy, isopropoxy, n-butoxy, isobutoxy, sec-butoxy, tert-butoxy, benzyloxy, tert-butyldimethylsilyloxy, methoxymethyloxy, and the like. Examples of cycloalkoxy include, but are not particularly limited to, cyclopropoxy, cyclopentoxy, cyclohexoxy, and the like. Examples of aryloxy include, but are not particularly limited to, phenoxy, naphthoxy, and substitution products thereof in which at least one hydrogen atom is substituted with a substituent, and the like. In this case, examples of the substituent include halogen atoms, nitro, nitrile, alkyl, cycloalkyl, alkenyl, cycloalkenyl, alkynyl, alkoxy, cycloalkoxy, and the like. Specific examples thereof are as described above.

Specific examples of the reaction substrates include the carbonyl compound represented by the above-described $R^a$—C(=O)—CH$_2$—R$^b$ or R$^a$—C(=O)—CH$_2$—C(=O)—R$^c$ in which R$^a$, R$^b$, and R$^c$ are each selected from substituents described below. That is, the carbonyl compound can be selected from compounds in which R$^a$ represents a hydrogen atom, methyl, tert-butoxy, phenyl, methylphenyl, ethylphenyl, halogenated phenyl, methoxyphenyl, biphenyl, methylimidazolyl, phenylimidazolyl, methoxy, pyridyl, benzyl or thienyl, R$^b$ represents a hydrogen atom, benzyl, phenyl, or a $C_1$-$C_{16}$ alkyl group (however, a phenyl group or alkyl group may be substituted by halogen (particularly, chlorine or bromine), phenyl, ethoxycarbonyl, benzyloxy, tert-butyldimethylsilyloxy, or methoxymethyloxy or may have a double bond), and R$^c$ represents a hydrogen atom, methyl, tert-butoxy, phenyl, methylphenyl, ethylphenyl, halogenated phenyl, methoxyphenyl, biphenyl, methylimidazolyl, phenylimidazolyl, methoxy, pyridyl, benzyl, or thienyl. Carbonyl compounds in which R$^a$, —R$^b$, and —C(=O)CH$_2$— are bonded to each other to form cycloalkane, for example, cyclohexane or cyclopentane may be used. Further, condensed-ring compounds each including the cycloalkane and an aromatic ring, for example, phenyl, may be used. The cycloalkane and the aromatic ring may have a substituent, for example, an alkyl group (particularly, a tert-butyl group) or halogen (particularly, bromine). Alternatively, R$^a$, —R$^b$, and —C(=O)CH$_2$— may be bonded to each other to form cyclic ether, for example, tetrahydropyrane.

In the method for producing an α-acyloxycarbonyl compound of the present invention, an additive may be used for accelerating the α-acyloxylation reaction or suppressing the production of by-products. The additive is preferably an amine and more preferably a primary or secondary amine. Specific examples thereof pyrrolidine, piperidine, 2,2,6,6-tetraalkylpiperidine, morpholine, 4-phenylbutylamine, and the like. These additives are particularly effective for the case of aldehyde used as the reaction substrate.

In addition, for example, when a synthetic intermediate of a natural product, a synthetic intermediate of a medicinal or agricultural product, or a monomer of a polymer has a carbonyl skeleton of any one of ketones, aldehydes, and esters, the synthetic intermediate or the monomer can also be used as the reaction substrate.

In the method for producing an α-acyloxycarbonyl compound of the present invention, the carboxylic acid serving as the other reaction substrate has very wide applicability. Carboxylic acids represented by $R^dCO_2H$ are preferred. Examples of R$^d$ include alkyl, cycloalkyl, alkenyl, cycloalkenyl, alkynyl, aryl, heterocycle, and the like, which, excluding a hydrogen atom, may have a substituent. Specific examples of the substituent are as described above. Typical examples of the carboxylic acid include saturated aliphatic carboxylic acids such as acetic acid, propanoic acid, butanoic acid, pentanoic acid, and the like; unsaturated aliphatic carboxylic acids such as acrylic acid, methacrylic acid, and the like; and aromatic carboxylic acids such as benzoic acid and the like. Among these, the unsaturated aliphatic carboxylic acids cause the intermolecular oxidative coupling reaction to proceed selectively and efficiently without oxidation of an unsaturated bond and proceeding of a polymerization reaction in spite of an oxidation reaction in the method for producing an α-acyloxycarbonyl compound of the present invention.

In the method for producing an α-acyloxycarbonyl compound of the present invention, the amounts of the carbonyl compound and carboxylic acid used may be appropriately determined in view of reactivity. The mixing ratio between the carboxylic acid and the carbonyl compound is preferably 0.5:2 to 2:0.5 and more preferably 1:2 to 2:1. From the economical viewpoint, the carboxylic acid is preferably used at 1 equivalent relative to the carbonyl compound. However, when the carboxylic acid is more expensive than the carbonyl compound or when reactivity is excellent in the presence of an excess of the carbonyl compound, the amount of the carboxylic acid used may be less than 1 equivalent relative to the carbonyl compound. Conversely, when the carbonyl compound is more expensive than the carboxylic acid or when reactivity is excellent in the presence of an excess of the carboxylic acid, the amount of the carboxylic acid used may be more than 1 equivalent relative to the carbonyl compound.

An α-acyloxycarbonyl compound of the present invention is represented by the following formula (1):

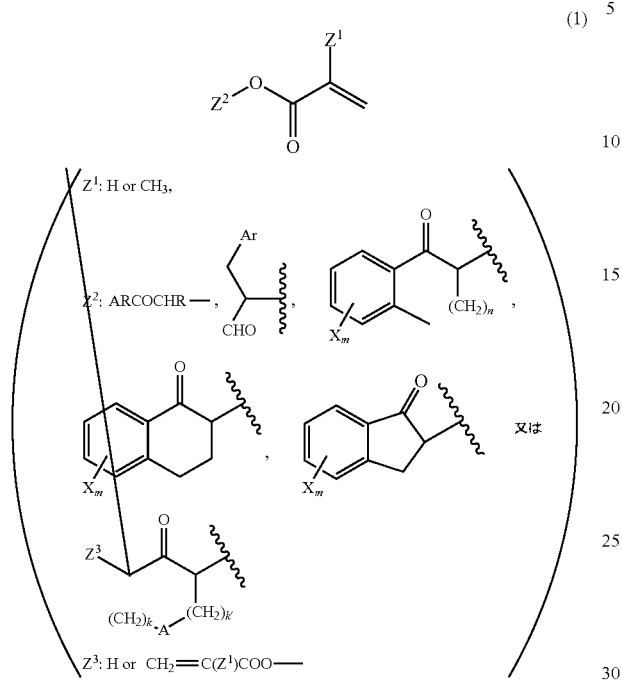

In this formula, Ar is a phenyl group, a phenyl group having one or more alkyl groups, or a phenyl group having one or more halogen atoms, R is an alkyl group, X is an alkyl group or a halogen atom, m is an integer of 0 to 4, n is an integer of 1 to 4, k and k' are each an integer of 0 to 4 and k+k' is an integer of 1 to 4, and A is O, S, NH, NR, or CHR (R is an alkyl group).

Examples of an alkyl group include alky groups which have 1 to 8 carbon atoms and may be branched, such as a methyl group, an ethyl group, a n-propyl group, an isopropyl group, a n-butyl group, an isobutyl group, a sec-butyl group, a tert-butyl group, and the like. Examples of a halogen atom include a fluorine atom, a chlorine atom, a bromine atom, an iodine atom, and the like. The above-described production method of the present invention is suitable for producing the α-acyloxycarbonyl compound represented by the formula (1). In addition, the α-acyloxycarbonyl compound of the formula (1) has an acrylic acid skeleton or methacrylic acid skeleton and is thus useful as a monomer for synthesizing a polymer. A polymer produced by polymerizing the monomer is expected to have high heat resistance or high refractive index or expected to suppress curing shrinkage.

Examples of the α-acyloxycarbonyl compound of the formula (1) include those represented by formulae below.

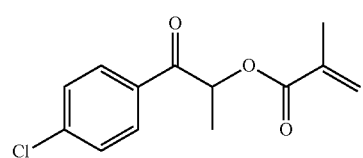

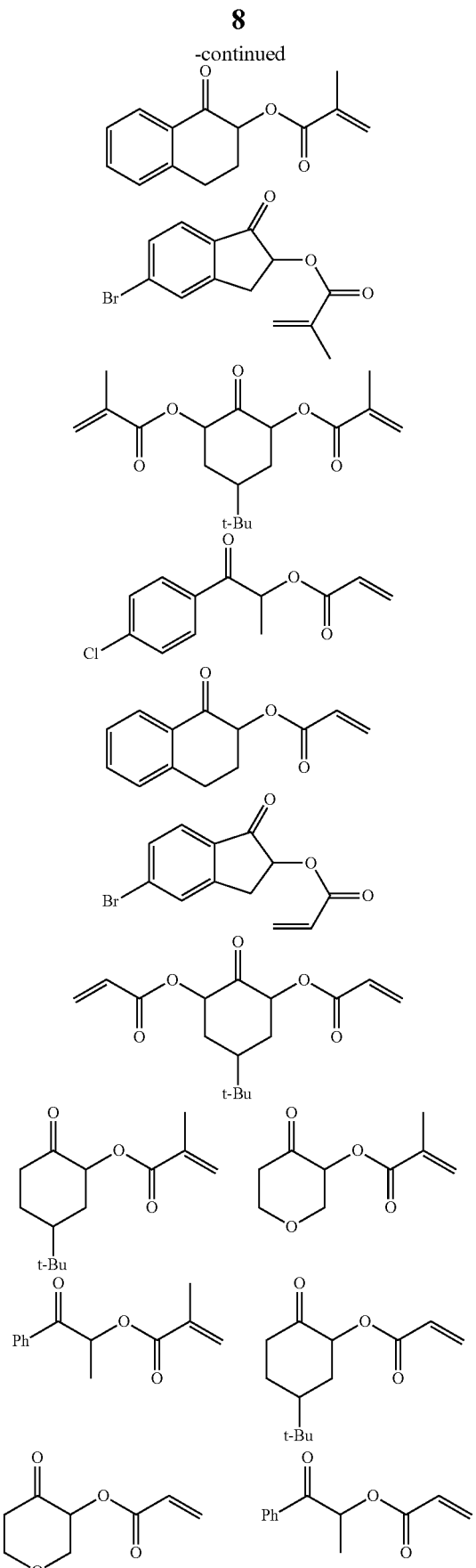

Of course, the present invention is not limited to the above-described embodiments and can be carried out in various modes within the technical scope of the present invention.

EXAMPLES

Example 1

Propiophenone (134 mg, 1.0 mmol), benzoic acid (61.1 mg, 0.5 mmol), and Bu$_4$NI (18.5 mg, 0.05 mmol, 10 mol % relative to benzoic acid) were dissolved in ethyl acetate (5 mL), and TBHP (5.5 M decane solution (manufactured by Aldrich); 0.18 mL, 1.0 mmol, 2 equivalents relative to benzoic acid) was added to the resultant solution at room temperature. The reaction mixture was stirred under heating for 24 hours in an oil bath at 75° C. After the completion of reaction, the reaction solution was cooled to room temperature and washed with an aqueous Na$_2$S$_2$O$_3$ solution and an aqueous NaHCO$_3$ solution. An aqueous layer was extracted with ethyl acetate, and an organic layer was washed with a saline solution and water. The resultant organic layer was dried with anhydrous Na$_2$SO$_4$. After the solvent was removed with an evaporator, an intended product, 2-benzoyloxy-1-phenyl-1-propane, was isolated by silica gel column chromatography (developing solvent, hexane:EtOAc=20:1 (v/v)) (126 mg, 0.495 mmol, yield 99%).

The spectral data of the resultant product was as follows: $^1$H NMR (CDCl$_3$, 400 MHz) δ 1.68 (d, J=6.9 Hz, 3H), 6.21 (q, J=6.9 Hz, 1H), 7.43-7.51 (m, 4H), 7.56-7.62 (m, 2H), 8.01 (d, J=6.9 Hz, 2H), 8.09 (d, J=7.3 Hz, 2H); $^{13}$C NMR (CDCl$_3$, 100 MHz) δ 17.1, 71.8, 128.3 (2C), 128.4 (2C), 128.7 (2C), 129.4, 129.7 (2C), 133.2, 133.5, 134.3, 165.8, 196.6

Example 2

A product was produced by the same method as in Example 1 except that in Example 1, 1.0 mmol of benzoic acid, 0.1 mmol (10 mol % relative to benzoic acid) of Bu$_4$NI, and 2.0 mmol (2 equivalents relative to benzoic acid) of TBHP were used and heated for 50 hours. The yield was 80%.

Example 3

A product was produced by the same method as in Example 1 except that in Example 1, 2.0 mmol of benzoic acid, 0.1 mmol (10 mol % relative to propiophenone) of Bu$_4$NI, and 2.0 mmol (2 equivalents relative to propiophenone) of TBHP were used and heated for 68 hours. The yield was 80%.

Example 4

A product was produced by the same method as in Example 1 except that in Example 1, 1 mmol of benzoic acid, 0.1 mmol (10 mol % relative to benzoic acid) of Bu$_4$NI, and 1.1 mmol (1.1 equivalents relative to benzoic acid) of TBHP were used and heated for 29 hours. The yield was 76%.

Example 5

A product was produced by the same method as in Example 4 except that in Example 4, 1.1 mmol (1.1 equivalents relative to benzoic acid) of TBHP (70% aqueous solution) was used in place of TBHP (5.5 M decane solution). The yield was 72%.

Example 6

A product was produced by the same method as in Example 1 except that in Example 1, 1.0 mmol of benzoic acid, 0.1 mmol (10 mol % relative to benzoic acid) of (C$_{18}$H$_{37}$)$_4$NI instead of Bu$_4$NI, and 2.0 mmol (2 equivalents relative to benzoic acid) of TBHP were used and heated for 47 hours. The yield was 92%. In addition, (C$_{18}$H$_{37}$)$_4$NI was prepared from (C$_{18}$H$_{37}$)$_4$NBr by an ordinary method.

Example 7

A product was produced by the same method as in Example 1 except that in Example 1, 1.0 mmol of benzoic acid, 0.1 mmol (10 mol % relative to benzoic acid) of Ph$_4$PI instead of Bu$_4$NI, and 2.0 mmol (2 equivalents relative to benzoic acid) of TBHP were used and heated for 52 hours. The yield was 76%.

Example 8

A product was produced by the same method as in Example 1 except that in Example 1, 1.0 mmol of benzoic acid, 0.1 mmol (10 mol % relative to benzoic acid) of Ph$_3$MePI instead of Bu$_4$NI, and 2.0 mmol (2 equivalents relative to benzoic acid) of TBHP were used. The yield was 76%.

Example 9

A product was produced by the same method as in Example 1 except that in Example 1, 0.05 mmol (10 mol % relative to benzoic acid) of KI instead of Bu$_4$NI and 0.05 mmol (10 mol % relative to benzoic acid) of 18-crown-6 were used. The yield was 84%. When 18-crown-16 was not used, activity was low because potassium iodide was not dissolved in the solvent.

The results of Examples 1 to 9 are shown in Table 1. The equivalent of the oxidizer and yield were calculated based on, of the ketone and the carboxylic acid, one having a smaller number of moles. Table 1 indicates that when ammonium iodide was used as the catalyst precursor, the reaction quantitatively proceeded at a ketone/carboxylic acid mixing ratio of 2:1 (Example 1), and the reaction efficiently proceeded even at a mixing ratio of 1:1 (Example 2) or 1:2 (Example 3). In addition, even when tetrabutylammonium iodide (Examples 1 to 5) or tetraoctadecylammonium iodide (Example 6) was used as the catalyst precursor, when tetraphenylphosphonium iodide (Example 7) or methyltriphenylphosphonium iodide (Example 8) was used as the catalyst precursor, and when an alkali metal iodide was used (Example 9), the reaction efficiently proceeded. Even when water was contained in the oxidizer (Example 5), the reaction proceeded to an extent comparable to the case where water was not contained (Example 4).

TABLE 1

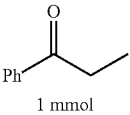

| | Catalyst precursor | x (mmol) | y[*1] (equiv) | State of TBHP | Conditions | Yield (%) |
|---|---|---|---|---|---|---|
| Example 1 | Bu$_4$NI | 0.5 | 2 | 5.5 M decane solution | 75° C., 24 h | 99 |
| Example 2 | Bu$_4$NI | 1 | 2 | 5.5 M decane solution | 75° C., 50 h | 80 |
| Example 3 | Bu$_4$NI | 2 | 2 | 5.5 M decane solution | 75° C., 68 h | 80 |
| Example 4 | Bu$_4$NI | 1 | 1.1 | 5.5 M decane solution | 75° C., 29 h | 76 |
| Example 5 | Bu$_4$NI | 1 | 1.1 | 70% aq. solution | 75° C., 29 h | 72 |
| Example 6 | (C$_{18}$H$_{37}$)$_4$NI | 1 | 2 | 5.5 M decane solution | 75° C., 47 h | 92 |
| Example 7 | Ph$_4$PI | 1 | 2 | 5.5 M decane solution | 75° C., 52 h | 76 |
| Example 8 | Ph$_3$MePI | 1 | 2 | 5.5 M decane solution | 75° C., 24 h | 76 |
| Example 9 | KI+ 18-Crown-6 | 0.5 | 2 | 5.5 M decane solution | 75° C., 24 h | 84 |

[*1]Amounts of catalyst precursor and TBP were calculated based on, of carbonyl compound and carboxylic acid, one having a smaller number of moles.

Although not shown in Table 1, when a water solution of hydrogen peroxide 300 ("%" is "% by mass") was used instead of TBHP, the yield was lower than that with TBHP, but the intended product could be produced. In addition, even when THF, 1,4-dioxane, diethyl ether, or acetonitrile was used as the reaction solvent, the intended product could be produced in yield equivalent to or slightly lower than that with ethyl acetate. When dichloroethane or toluene was used as the reaction solvent, the intended product was produced, but the yield was lower than in the use of ethyl acetate. Table 2 shows the results of reaction using various solvents according to Example 1. However, the reaction temperature was 50° C., not 75° C. In Example 10, the reaction temperature is 50° C. lower than 75° C. in Example 3, and the yield is decreased accordingly. Although, in Example 10, ethyl acetate was used as the solvent, the intended product could be produced in the same or slightly lower yield even by changing the solvent to THF (Example 11), acetonitrile (Example 12), or diethyl ether (Example 13). This reveals that like ethyl acetate, the solvents used in Examples 11 to 13 are suitable for this reaction.

TABLE 2

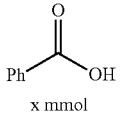

| | Catalyst precursor | Conditions | Yield (%) |
|---|---|---|---|
| Example 10 | Bu$_4$NI | EtOAc, 50° C., 24 h | 39 |
| Example 11 | Bu$_4$NI | THF, 50° C., 24 h | 38 |
| Example 12 | Bu$_4$NI | CH$_3$CN, 50° C., 24 h | 29 |
| Example 13 | Bu$_4$NI | Et$_2$O, 50° C., 24 h | 34 |

Examples 14 to 42

An intermolecular oxidative coupling reaction between a carbonyl compound and a carboxylic acid was variously examined. In these examples, carbonyl compound R$^1$C(=O)CH$_2$R$^2$ and carboxylic acid R$^3$COOH were used so as to produce products shown in Tables 3 and 4, and the reaction was performed according to Example 1 using numbers of moles of carboxylic acid under reaction conditions shown in Tables 3 and 4. The results are shown in Tables 3 and 4. The equivalents of the oxidizer and yields were calculated based on, of the ketone and the carboxylic acid, one having a smaller number of moles.

As in Examples 14 to 24, even when a substituent (R) of a propiophenone benzene ring was either an electron-donating group or an electron-withdrawing group, the reaction efficiently proceeded. In particular, in Examples 16 and 18, the reaction substantially quantitatively proceeded even at 50° C. As in Examples 25 and 26, even when a substituent (R) of a benzoic acid benzene ring was either an electron-donating group or an electron-withdrawing group, the reaction efficiently proceeded. In addition, as in Examples 27 and 28, even when an imidazol-2-yl group, which can be easily deprotected, was introduced as a group adjacent to carbonyl carbon in the substrate, the reaction efficiently proceeded. As in Examples 29 to 35, the product could be produced in high yield not only with an aromatic carboxylic acid but also with a saturated aliphatic carboxylic acid or unsaturated aliphatic carboxylic acid. In particular, with any one of acrylic acid (Examples 32 and 33) and methacrylic acid (Examples 34 and 35), which are polymerizable unsaturated aliphatic carboxylic acids, the intermolecular oxidative coupling reaction, not polymerization reaction, proceeded selectively and efficiently. Further, even when as in Examples 36 to 38, butylphenyl ketone or chloropropylphenyl ketone was used in place of propiophenone, when as in Example 39, a cyclic aliphatic ketone was used, and when as in Examples 40 and 41, a 1,3-diketone or 1,3-diester was used, the reaction relatively efficiently proceeded. It was interesting that even when as in Example 42, an aldehyde was used, the reaction rapidly proceeded, and the intended product could be produced in high yield. Although not shown in Table 3 and 4, when acetophenone was used in place of propiophenone, the intended product was produced in low yield.

TABLE 3

| Product | | R | x (mmol) | Conditions | Yield (%) |
|---|---|---|---|---|---|
| Example 14 | | F | 0.5 | EtOAc, 75° C., 24 h | 99 |
| Example 15 | | F | 1 | EtOAc, 75° C., 26 h | 90 |
| Example 16 | | Cl | 0.5 | EtOAc, 75° C., 24 h | 99 |
| Example 17 | | Cl | 1 | EtOAc, 75° C., 23 h | 93 |
| Example 18 | | Br | 0.5 | EtOAc, 75° C., 24 h | 99 |
| Example 19 | | Br | 1 | EtOAc, 75° C., 24 h | 74 |
| Example 20 | | Ph | 0.5 | EtOAc, 75° C., 24 h | 99 |
| Example 21 | | Ph | 1 | EtOAc, 75° C., 22 h | 92 |
| Example 22 | | Me | 0.5 | EtOAc, 75° C., 24 h | 81 |
| Example 23 | | OMe | 0.5 | EtOAc, 75° C., 32 h | 82 |
| Example 24 | | OMe | 1 | EtOAc, 75° C., 5 d | 58 |
| Example 25 | | Me | 0.5 | EtOAc, 75° C., 23 h | 91 |
| Example 26 | | $NO_2$ | 0.5 | EtOAc, 75° C., 53 h | 85 |
| Example 27 | | Me | 0.5 | EtOAc, 75° C., 24 h | 88[*1] |
| Example 28 | | Ph | 0.5 | EtOAc, 75° C., 24 h | 99[*1] |

[*1] Yield was obtained by NMR analysis of reaction mixture after completion of reaction.

TABLE 4
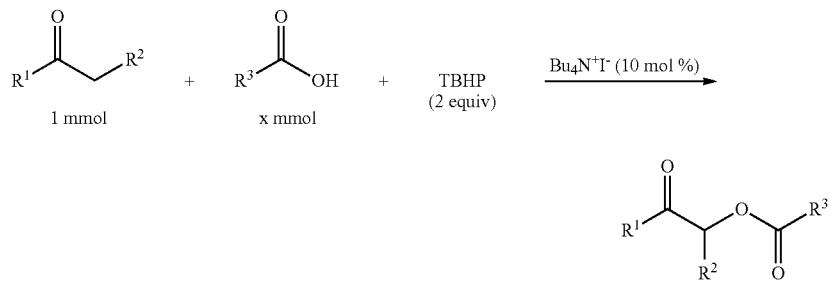
| | Product | x (mmol) | Conditions | Yield (%) |
|---|---|---|---|---|
| Example 29 | 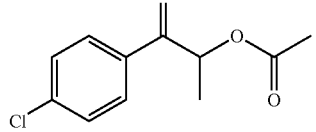 | 0.5 | EtOAc, 75° C., 24 h | 78 |
| Example 30 | | 1 | EtOAc, 75° C., 24 h | 70 |
| Example 31 | 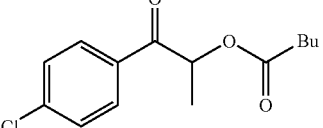 | 0.5 | EtOAc, 75° C., 16 h | 99 |
| Example 32 | 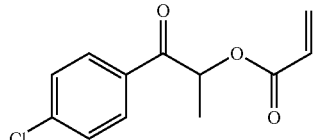 | 0.5 | EtOAc, 75° C., 24 h | 88 |
| Example 33 | | 1 | EtOAc, 75° C., 24 h | 67 |
| Example 34 | 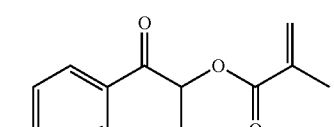 | 0.5 | EtOAc, 75° C., 24 h | 73 |
| Example 35 | | 1 | EtOAc, 75° C., 9 h | 67 |
| Example 36 | 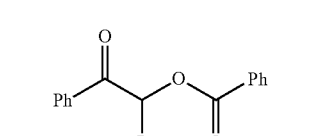 | 0.5 | EtOAc, 75° C., 24 h | 99 |
| Example 37 | | 1 | EtOAc, 75° C., 30 h | 78 |
| Example 38 | 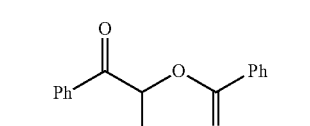 | 0.5 | EtOAc, 75° C., 24 h | 71 |
| Example 39 | 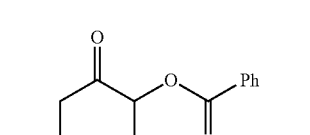 | 0.5 | EtOAc, 75° C., 27 h | 61 |
| Example 40 | 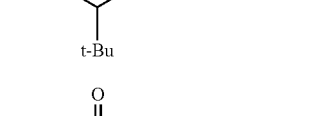 | 0.5 | EtOAc, 75° C., 24 h | 76 |

TABLE 4-continued

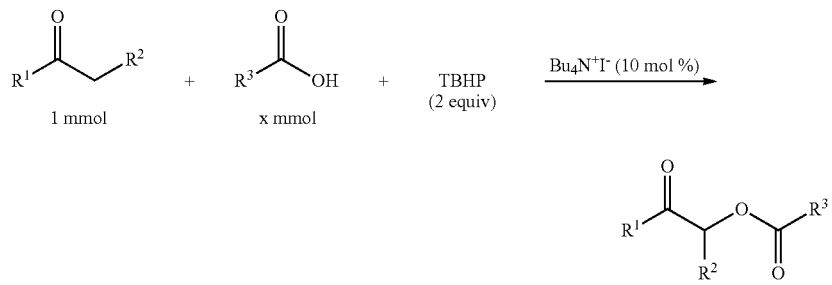

| | Product | x (mmol) | Conditions | Yield (%) |
|---|---|---|---|---|
| Example 41 | 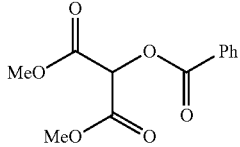 [SMILES: COC(=O)C(OC(=O)c1ccccc1)C(=O)OC] | 0.5 | EtOAc, 75° C., 24 h | 51 |
| Example 42 | 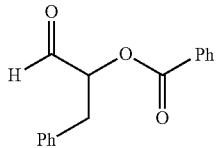 [SMILES: O=CC(Cc1ccccc1)OC(=O)c1ccccc1] | 1 | EtOAc, 75° C., 20 h | 67 |

The spectral data of the products obtained in Examples 14-42 are as follows.

The product obtained in Examples 14, 15: $^1$H NMR (CDCl$_3$, 400 MHz) δ 1.67 (d, J=6.8 Hz, 3H), 6.15 (q, J=6.8 Hz, 1H), 7.16 (t, J=8.3 Hz, 2H), 7.45 (t, J=7.6 Hz, 2H), 7.58 (t, J=7.6 Hz, 1H), 8.00-8.09 (m, 4H).

The product obtained in Examples 16, 17: $^1$H NMR (CDCl$_3$, 300 MHz) δ 1.66 (d, J=6.9 Hz, 3H), 6.13 (q, J=6.9, 1H), 7.43-7.48 (m, 4H), 7.59 (t, J=7.3 Hz, 1H), 7.95 (d, J=7.3 Hz, 2H), 8.08 (d, J=6.8 Hz, 2H).

The product obtained in Examples 18, 19: $^1$H NMR (CDCl$_3$, 400 MHz) δ 1.66 (d, J=6.9 Hz, 3H), 6.12 (q, J=6.9 Hz, 1H), 7.45 (t, J=7.8 Hz, 2H), 7.59 (t, J=7.8 Hz, 1H), 7.63 (t, J=8.7 Hz, 2H), 7.87 (d, J=8.7 Hz, 2H), 8.08 (d, J=7.8 Hz, 2H).

The product obtained in Examples 20, 21: $^1$H NMR (CDCl$_3$, 400 MHz) δ 1.71 (d, J=6.8 Hz, 3H), 6.24 (q, J=6.8 Hz, 1H), 7.39-7.50 (m, 5H), 7.56-7.64 (m, 3H), 7.71 (d, J=8.7 Hz, 2H), 8.07-8.12 (m, 4H); $^{13}$C NMR (CDCl$_3$, 100 MHz) δ 17.2, 71.9, 127.3 (2C), 127.4 (2C), 128.3, 128.4 (2C), 128.9 (2C), 129.1 (2C), 129.5, 129.9 (2C), 133.1, 133.3, 139.7, 146.2, 166.0, 196.2.

The product obtained in Example 22: $^1$H NMR (CDCl$_3$, 400 MHz) δ 1.66 (d, J=6.9 Hz, 3H), 2.42 (s, 3H), 6.20 (q, J=6.9 Hz, 1H), 7.29 (d, J=8.2 Hz, 2H), 7.47 (t, J=7.3 Hz, 2H), 7.58 (d, J=7.3 Hz, 1H), 7.91 (d, J=8.2 Hz, 2H), 8.10 (d, J=7.3 Hz, 2H).

The product obtained in Examples 23, 24: $^1$H NMR (CDCl$_3$, 400 MHz) δ 1.67 (d, J=6.9 Hz, 3H), 3.88 (s, 3H), 6.18 (q, J=6.9 Hz, 1H), 6.96 (d, J=8.7 Hz, 2H), 7.45 (t, J=7.6 Hz, 2H), 7.57 (t, J=7.6 Hz, 1H), 8.00 (d, J=8.7 Hz, 2H), 8.10 (d, J=7.6 Hz, 2H).

The product obtained in Example 25: $^1$H NMR (CDCl$_3$, 400 MHz) δ 1.68 (d, J=6.9 Hz, 3H), 2.41 (s, 3H), 6.19 (q, J=6.9 Hz, 1H), 7.23-7.26 (m, 2H), 7.48 (t, J=7.3 Hz, 2H), 7.59 (t, J=7.3 Hz, 1H), 7.95-8.01 (m, 4H).

The product obtained in Example 26: $^1$H NMR (CDCl$_3$, 400 MHz) δ 1.71 (d, J=6.9 Hz, 3H), 6.25 (q, J=6.9 Hz, 1H), 7.52 (t, J=7.3 Hz, 2H), 7.63 (t, J=7.3 Hz, 1H), 8.00 (d, J=8.7 Hz, 1H), 8.26-8.31 (m, 4H).

The product obtained in Example 27: $^1$H NMR (CDCl$_3$, 400 MHz) δ 1.76 (d, J=6.9 Hz, 3H), 4.01 (s, 3H), 6.40 (q, J=6.9 Hz, 1H), 7.07 (s, 1H), 7.21 (s, 1H), 7.45 (t, J=7.8 Hz, 2H), 7.58 (t, J=7.8 Hz, 1H), 8.12 (d, J=7.8 Hz, 2H).

The product obtained in Example 28: $^1$H NMR (CDCl$_3$, 400 MHz) δ 1.78 (d, J=7.3 Hz, 3H), 6.41 (q, J=7.3 Hz, 1H), 7.14-7.50 (m, 10H), 8.06 (d, J=7.3 Hz, 2H).

The product obtained in Examples 29, 30: $^1$H NMR (CDCl$_3$, 400 MHz) δ 1.52 (d, J=6.9 Hz, 3H), 2.14 (s, 3H), 5.89 (q, J=6.9 Hz, 1H), 7.45 (dt, J=2.3, 8.7 Hz, 2H), 7.88 (dt, J=2.3, 8.7 Hz, 2H).

The product obtained in Example 31: $^1$H NMR (CDCl$_3$, 400 MHz) δ 0.96 (t, J=7.3 Hz, 3H), 1.51 (d, J=7.3 Hz, 3H), 1.62-1.72 (m, 2H), 2.38 (dt, J=2.3, 7.3 Hz, 2H), 5.90 (q, J=7.3 Hz, 1H), 7.45 (d, J=8.7 Hz, 2H), 7.88 (d, J=8.7 Hz, 2H).

The product obtained in Examples 32, 33: $^1$H NMR (CDCl$_3$, 400 MHz) δ 1.56 (d, J=7.3 Hz, 3H), 5.92 (dd, J=1.4, 10.5 Hz, 1H), 5.98 (q, J=6.9 Hz, 1H), 6.20 (dd, J=10.5, 17.4 Hz, 1H), 6.46 (dd, J=1.4, 17.4 Hz, 1H), 7.45 (d, J=8.2 Hz, 2H), 7.90 (d, J=8.2 Hz, 2H); $^{13}$C NMR (CDCl$_3$, 100 MHz) δ 16.8, 71.2, 127.4, 129.0 (2C), 129.7 (2C), 131.8, 132.5, 139.8, 165.2, 195.4.

The product obtained in Examples 34, 35: $^1$H NMR (CDCl$_3$, 400 MHz) δ 1.56 (d, J=6.9 Hz, 3H), 1.96 (s, 3H), 5.65 (s, 1H), 5.94 (q, J=6.9 Hz, 1H), 6.21 (s, 1H), 7.45 (d, J=8.2 Hz, 2H), 7.90 (d, J=8.2 Hz, 2H); $^{13}$C NMR (CDCl$_3$, 100 MHz) δ 16.8, 18.0, 71.4, 126.5, 128.9 (2C), 129.7 (2C), 132.6, 135.3, 139.8, 166.5, 195.6.

The product obtained in Examples 36, 37: $^1$H NMR (CDCl$_3$, 400 MHz) δ 1.00 (t, J=7.3 Hz, 3H), 1.53-1.63 (m, 2H), 1.96-2.02 (m, 2H), 6.12 (dd, J=5.0, 7.8 Hz, 1H), 7.44-7.51 (m, 4H), 7.56-7.62 (m, 2H), 8.05 (d, J=8.7 Hz, 2H), 8.10 (d, J=7.3 Hz, 2H).

The product obtained in Example 38: $^1$H NMR (CDCl$_3$, 400 MHz) δ 2.43-2.48 (m, 2H), 3.74-3.86 (m, 2H), 6.38 (t, J=6.4 Hz, 1H), 7.44-7.54 (m, 4H), 7.58-7.64 (m, 2H), 8.04 (d, J=7.3 Hz, 2H), 8.09 (d, J=7.3 Hz, 2H); $^{13}$C NMR (CDCl$_3$, 100 MHz) δ34.1, 40.6, 72.3, 128.3 (2C), 128.4 (2C), 128.8 (2C), 129.0, 129.7 (2C), 133.4, 133.8, 134.0, 165.7, 1952.

The product obtained in Example 39: $^1$H NMR (CDCl$_3$, 400 MHz) δ 0.97 (s, 9H), 1.4-1.50 (m, 1H), 1.69-1.82 (m, 2H), 2.13-2.18 (m, 1H), 2.42-2.58 (m, 3H), 5.45 (dd, J=6.4, 11.9 Hz, 1H), 7.48 (t, J=8.2 Hz, 2H), 7.57 (t, J=8.2 Hz, 1H), 8.09 (d, J=8.2 Hz, 2H).

The product obtained in Example 40 (mixed with keto-enole tautomer): $^1$H NMR (CDCl$_3$, 400 MHz) δ 2.07 (s, 3H, enol), 2.41 (s, 3H, ketone), 5.73 (s, 1H, ketone), 7.48-7.54 (m, 2H), 7.62-7.68 (m, 1H), 8.12 (dd, J=0.9, 8.3 Hz, ketone), 8.19 (dd, J=0.9, 8.3 Hz, enol).

The product obtained in Example 41: $^1$H NMR (CDCl$_3$, 400 MHz) δ 3.88 (s, 6H), 5.81 (s, 1H), 7.48 (t, J=7.8 Hz, 2H), 7.62 (t, J=7.8 Hz, 1H), 8.15 (d, J=7.8 Hz, 2H).

The product obtained in Example 42: $^1$H NMR (CDCl$_3$, 400 MHz) δ 3.20 (dd, J=8.2, 14.7 Hz, 1H), 3.30 (dd, J=4.6, 14.7 Hz, 1H), 5.43 (dd, J=4.6, 8.2 Hz, 1H), 7.23-7.34 (m, 5H), 7.45 (t, J=7.3 Hz, 2H), 7.60 (t, J=7.3 Hz, 1H), 8.03 (d, J=7.3 Hz, 2H), 9.67 (s, 1H); $^{13}$C NMR (CDCl$_3$, 100 MHz) δ 35.1, 79.0, 127.0, 128.4 (2C), 128.5 (2C), 128.9, 129.3 (2C), 129.6 (2C), 133.4, 135.3, 165.8, 198.0.

Examples 43 to 50

An intermolecular oxidative coupling reaction between a carbonyl compound and a carboxylic acid was variously examined. In the examples, carbonyl compound R$^1$C(=O)CH$_2$R$^2$ and carboxylic acid R$^3$CO$_2$H were used so as to produce products shown in Table 5, and the reaction was performed according to Example 1 under reaction conditions shown in Table 5. The results are shown in Table 5. The equivalent of the oxidizer and yield were calculated based on, of the ketone and the carboxylic acid, one having a smaller number of moles.

As in Examples 43 and 44, even when a ketone having a heterocycle was used as the carbonyl compound and benzoic acid was used as the carboxylic acid, the reaction efficiently proceeded. As in Examples 45 and 46, even when a 1,3-diketone or 1,3-ketoester was used as the carbonyl compound and benzoic acid was used as the carboxylic acid, the reaction efficiently proceeded. As in Examples 47 to 50, even when propiophenone was used as the carbonyl compound and acrylic acid or methacrylic acid was used as the carboxylic acid, like in Examples 32 to 35, the intermolecular oxidative coupling reaction selectively and efficiently proceeded without oxidation of an unsaturated bond of acrylic acid or methacrylic acid and a polymerization reaction of acrylic acid or methacrylic acid.

TABLE 5

$$R^1\overset{O}{-}CH_2R^2 \text{ (x equiv)} + R^3\overset{O}{-}OH \text{ (1 equiv)} + TBHP \text{ (2 equiv)} \xrightarrow{Bu_4N^+I^- \text{ (10 mol \%)}}_{EtOAc}$$

$$R^1\overset{O}{-}\underset{R^2}{\overset{}{C}H}-O-\overset{O}{C}-R^3$$

| | Product | x (equiv) | Conditions | Yield (%) |
|---|---|---|---|---|
| Example 43 | pyridin-2-yl-C(=O)-CH(CH$_3$)-OC(=O)Ph | 1.2 | 75° C., 48 h | 64 |
| Example 44 | thiophen-2-yl-C(=O)-CH(CH$_3$)-OC(=O)Ph | 1.0 | 75° C., 24 h | 79 |
| Example 45 | Ph-C(=O)-CH(OCOPh)-C(=O)-CH$_3$ | 1.0 | 50° C., 4 h | 78 |
| Example 46 | CH$_3$-C(=O)-CH(OCOPh)-C(=O)-O$^t$Bu | 1.0 | rt, 17 h | 83 |

TABLE 5-continued

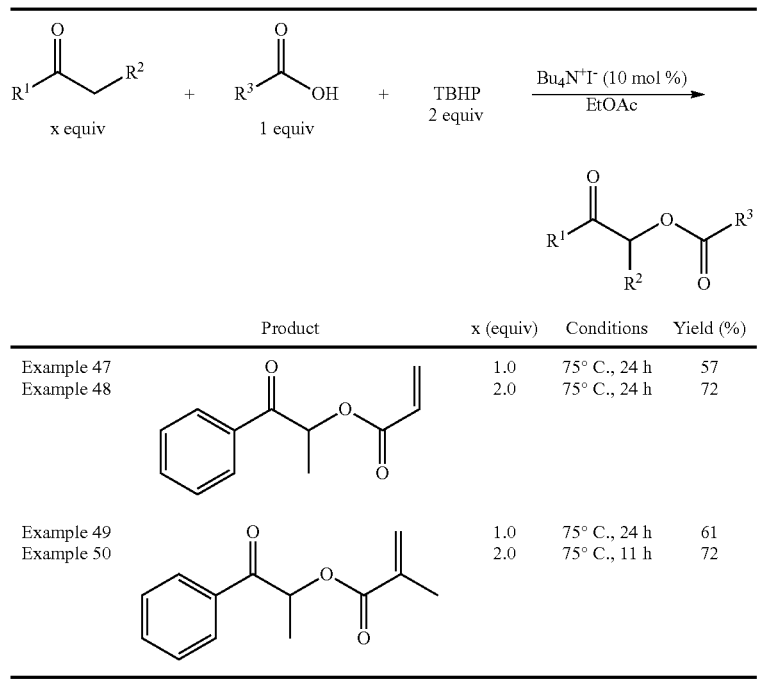

| | Product | x (equiv) | Conditions | Yield (%) |
|---|---|---|---|---|
| Example 47 | | 1.0 | 75° C., 24 h | 57 |
| Example 48 | | 2.0 | 75° C., 24 h | 72 |
| Example 49 | | 1.0 | 75° C., 24 h | 61 |
| Example 50 | | 2.0 | 75° C., 11 h | 72 |

The spectral data of the products obtained in Examples 43-50 are as follows.

The product obtained in Example 43: TLC, $R_f$=0.25 (hexane-EtOAc=4:1); IR (neat) 3060, 1710, 1451, 1272, 1117, 976 cm$^{-1}$; $^1$H NMR (CDCl$_3$, 400 MHz) δ 1.75 (d, J=7.4 Hz, 3H), 6.65 (q, J=7.4 Hz, 1H), 7.43-7.49 (m, 2H), 7.52 (ddd, J=1.4, 4.6, 7.8 Hz, 1H), 7.55-7.61 (m, 1H), 7.87 (dt, J=1.8, 7.8 Hz, 1H), 8.08-8.14 (m, 3H), 8.71-8.74 (m, 1H); $^{13}$C NMR (CDCl$_3$, 100 MHz) δ 16.9, 72.1, 122.7, 127.6, 128.3, 129.6, 129.8, 133.1, 137.0, 148.9, 151.3, 166.0, 197.2; HRMS (FAB+) m/z calcd for C$_{15}$H$_{14}$NO$_3$ (M+H) 256.0974. found 256.0977.

The product obtained in Example 44: TLC, $R_f$=0.29 (hexane-EtOAc=4:1); IR (CHCl$_3$) 3020, 1719, 1674, 1415, 1271, 1115 cm$^{-1}$; $^1$H NMR (CDCl$_3$, 400 MHz) δ 1.72 (d, J=7.0 Hz, 3H), 5.97 (q, J=7.0 Hz, 1H), 7.16 (dd, J=4.0, 5.0 Hz, 1H), 7.44-7.49 (m, 2H), 7.56-7.62 (m, 1H), 7.70 (dd, J=1.4, 5.0 Hz, 1H), 7.88 (dd, J=1.4, 4.0 Hz, 1H), 8.09-8.13 (m, 2H); $^{13}$C NMR (CDCl$_3$, 100 MHz) δ 17.5, 72.7, 128.1, 128.2, 129.1, 129.6, 132.6, 133.2, 134.4, 140.2, 165.6, 189.4; HRMS (FAB+) m/z calcd for C$_{14}$H$_{13}$O$_3$S (M+H) 261.0585. found 261.0582.

The product obtained in Example 45: TLC, $R_f$=0.34 (hexane-EtOAc=4:1); IR (neat) 3060, 1727, 1691, 1450, 1275, 1115 cm$^{-1}$; $^1$H NMR (keto and enol tautomers, CDCl$_3$, 400 MHz) δ 2.20 (s, 3H, enol), 2.41 (s, 3H, keto), 6.49 (s, 1H, keto), 7.30-7.35 (m, 2H, enol), 7.37-7.42 (m, 1H, enol), 7.45-7.55 (m, 4H, keto; 2H, enol), 7.60-7.67 (m, 2H, keto and enol), 7.77-7.81 (m, 2H, enol), 8.07-8.13 (m, 4H, keto, 2H, enol), 15.24 (s, 1H, enol); $^{13}$C NMR (keto and enol tautomers, CDCl$_3$, 100 MHz) δ 22.3, 26.9, 82.3, 127.3, 128.0, 128.2, 128.4, 128.5, 128.7, 129.4, 129.9, 130.0, 131.4, 133.0, 133.8, 133.9, 134.1, 134.2, 164.8, 165.0, 175.0, 190.8, 191.7, 199.5; HRMS (FAB+) m/z calcd for C$_{17}$H$_{15}$O$_4$ (M+H) 283.0970. found 283.0966.

The product obtained in Example 46: TLC, $R_f$=0.37 (hexane-EtOAc=4:1); $^1$H NMR (CDCl$_3$, 400 MHz) δ 1.52 (s, 9H), 2.43 (s, 3H), 5.63 (s, 1H), 7.45-7.51 (m, 2H), 7.59-7.64 (m, 1H), 8.11-8.16 (m, 2H); $^{13}$C NMR (CDCl$_3$, 100 MHz) δ 27.3, 27.7, 78.5, 83.9, 128.4, 128.5, 129.9, 133.7, 163.2, 165.0, 197.8.

The product obtained in Examples 47, 48: TLC, $R_f$=0.37 (hexane-EtOAc=4:1); IR (neat) 2990, 1726, 1698, 1408, 1196, 971 cm$^{-1}$; $^1$H NMR (CDCl$_3$, 400 MHz) δ 1.58 (d, J=6.9 Hz, 3H), 5.90 (dd, J=1.4, 10.4 Hz, 1H), 6.06 (q, J=6.9 Hz, 1H), 6.22 (dd, J=10.4, 17.4 Hz, 1H), 6.22 (dd, J=1.4, 17.4 Hz, 1H), 7.46-7.52 (m, 2H), 7.57-7.63 (m, 1H), 7.94-7.98 (m, 2H); $^{13}$C NMR (CDCl$_3$, 100 MHz) δ 17.0, 71.4, 127.6, 128.4, 128.7, 131.8, 133.5, 134.2, 165.3, 196.6; HRMS (FAB+) m/z calcd for C$_{12}$H$_{13}$O$_3$ (M+H) 205.0865. found 205.0864.

The product obtained in Examples 49, 50: TLC, $R_f$=0.29 (hexane-EtOAc=8:1); IR (neat) 2988, 1719, 1698, 1450, 1166, 971 cm$^{-1}$; $^1$H NMR (CDCl$_3$, 400 MHz) δ 1.58 (d, J=6.8 Hz, 3H), 1.97 (s, 3H), 5.64 (s, 1H), 6.01 (q, J=6.8 Hz, 1H), 6.22 (s, 1H), 7.46-7.51 (m, 2H), 7.57-7.62 (m, 1H), 7.94-7.98 (m, 2H); $^{13}$C NMR (CDCl$_3$, 100 MHz) δ 17.0, 18.1, 71.5, 126.4, 128.3, 128.6, 133.4, 134.3, 135.5, 166.6, 196.8; HRMS (FAB+) m/z calcd for C$_{13}$H$_{15}$O$_3$ (M+H) 219.1021. found 219.1018

Examples 51 to 61

An intermolecular oxidative coupling reaction between an aldehyde and a carboxylic acid was performed at a reaction temperature of 50° C. according to Example 1 and according to a reaction formula under reaction conditions shown in Table 6. The results are shown in Table 6. In the reaction formula shown in Table 6, "EtOAc (0.2 M)" represents the number of moles of aldehyde per volume of ethyl acetate. In addition, main by-products were a self-aldol condensation product and an oxidative dehydrogenation product (3-phenyl-2-pentenal).

When acetic acid was used as the carboxylic acid, in an example in which amine was not added as in Example 51, the yields of the intended product and by-products after the reaction for 30 hours were 60% and about 20%, respectively. In contrast, when pyrrolidine (Examples 52 to 54) or piperidine (Examples 55 to 57) was added, there was found the tendency to improve the yield of the intended product and suppress the production of by-products. The effect of suppressing the production of by-products was significantly observed with an adding amount of 2 to 5 equivalents, particularly 2 equivalents, relative to aldehyde. Also, when 2,2,6,6-tetramethylpiperidine (Example 58) or morpholine (Example 59) was added as an additive at 2 equivalents relative to aldehyde, the effect of suppressing the production of by-products was observed. Although, in Example 58, the yield of the intended product seems to be decreased, the yield of the intended product is expected to be improved by extending the reaction time because of the small amount of by-products. In Examples 52 to 59, a secondary amine was used as an additive, while in Example 60, a primary amine was used as an additive. In this case, the same tendency as that of a secondary amine was observed, but the effect was lower than that of the secondary amine.

When benzoic acid was used as the carboxylic acid, in an example in which an amine was not added as in the above-described Example 42, the yield after the reaction for 20 hours was 67%, and many by-products were present. On the other hand, by adding piperidine (Example 61), the yield of the intended product was significantly improved to 94%, and the production of by-products was greatly suppressed. In addition, the isolated yield was also as high as 89%.

TABLE 6

Ph-CH2-CH2-CHO (1 equiv) + R-C(O)-OH (x equiv) + TBHP (y equiv) → [Bu4N+I- (10 mol %), EtOAc (0.2 M), 50° C.] → Ph-CH2-CH(OCOR)-CHO (Intended product)

| | Carboxylic acid | | | Additive | | Reaction | Yield (%)[*1] | |
| --- | --- | --- | --- | --- | --- | --- | --- | --- |
| | R | x | y | Formula | mol % | time | Intended product | by-product |
| Example 51 | Me | 1 | 2 | — | — | 30 h | 60 | ca. 20 |
| Example 52 | Me | 1 | 1.1 | pyrrolidine | 10 | 20 h | 68 | ca. 30 |
| Example 53 | Me | 1 | 1.1 | pyrrolidine | 5 | 17 h | 77 | ca. 15 |
| Example 54 | Me | 1 | 1.1 | pyrrolidine | 2 | 17 h | 75 | ca. 10 |
| Example 55 | Me | 1 | 1.1 | piperidine | 10 | 5 h | 78[74][*2] | ca. 15 |
| Example 56 | Me | 1 | 1.1 | piperidine | 5 | 5 h | 80[72][*2] | ≤5 |
| Example 57 | Me | 1 | 1.1 | piperidine | 2 | 5 h | 73 | <5 |
| Example 58 | Me | 2 | 1.3 | 2,2,6,6-tetramethylpiperidine | 2 | 10 h | 46 | <5 |
| Example 59 | Me | 2 | 1.1 | morpholine | 2 | 19 h | 78 | ca. 10 |
| Example 60 | Me | 1 | 1.1 | Ph(CH2)3NH2 | 2 | 9 h | 53 | ca. 15 |
| Example 42 | Ph | 1 | 2 | — | — | 20 h[*3] | 67 | many |

TABLE 6-continued

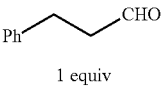

| | Carboxylic acid | | Additive | | Reaction | Intended | by- |
|---|---|---|---|---|---|---|---|
| | R | x | y | Formula | mol % | time | product | product |
| Example 61 | Ph | 1 | 1.1 | 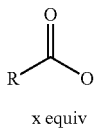 | 2 | 5 h | 94[89][*2] | <5 |

[*1] Yield was obtained by NMR analysis of reaction mixture after completion of reaction.
[*2] Value shown in parenthesis is isolation yield of intended product.
[*3] Reaction temperature was 75° C.

The spectral data of the products obtained in Examples 51-60 are as follows.

The product obtained in Examples 51-60: TLC, $R_f$=0.46 (hexane-EtOAc=1:1); IR (neat) 3020, 1739, 1373, 1216 1033 cm$^{-1}$; $^1$H NMR (CDCl$_3$, 400 MHz) δ 2.13 (s, 3H), 3.02 (dd, J=8.7, 14.6 Hz, 1H), 3.18 (dd, J=4.8, 14.6 Hz, 1H), 5.23 (dd, J=4.8, 8.7 Hz, 1H), 7.18-7.35 (m, 5H), 9.56 (s, 1H); $^{13}$C NMR (CDCl$_3$, 100 MHz) δ 20.6, 35.0, 78.6, 127.1, 128.6, 129.3, 135.4, 170.4, 198.0; HRMS (FAB+) m/z calcd for C$_{11}$H$_{13}$O$_3$ (M+H) 193.0865. found 193.0868.

Examples 62 to 72

An intermolecular oxidative coupling reaction between an aldehyde and a carboxylic acid was performed using piperidine as an additive. That is, according to Example 1, the reaction was performed using aldehyde R$^1$CH$_2$CH$_2$CHO and carboxylic acid R$^2$CO$_2$H so as to produce products shown in Table 7 in the presence of piperidine under reaction conditions shown in Table 7. The results are shown in Table 7.

As in Examples 62 to 72, even when any one of various aldehydes was used as the carbonyl compound, the reaction efficiently proceeded. In particular, as in Examples 62 and 63, even when acrylic acid or methacrylic acid was used as the carboxylic acid, like in Examples 32 to 35 and 47 to 50, the intermolecular oxidative coupling reaction selectively and efficiently proceeded without oxidation of an unsaturated bond of acrylic acid or methacrylic acid and a polymerization reaction of acrylic acid or methacrylic acid.

TABLE 7

| | x (mol %) | y (mol %) | Product | Reaction time | Yield (%) |
|---|---|---|---|---|---|
| Example 62 | 20 | 5 | 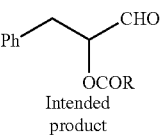 | 4 h | 62% |

TABLE 7-continued $$R^1\diagdown\diagdown^{CHO} + R^2CO_2H + TBHP \xrightarrow[\text{EtOAc, 50°C}]{\text{Bu}_4\text{N}^+\text{I}^- \text{ (x mol)}\\ \text{Piperidine (y mol \%)}} R^1\diagdown\diagup^{CHO}_{OCOR^2}$$

1 equiv | 1 equiv | 1.1 equiv

| | x (mol %) | y (mol %) | Product | Reaction time | Yield (%) |
|---|---|---|---|---|---|
| Example 63 | 10 | 5 | Ph-CH₂-CH(OC(O)C(CH₃)=CH₂)-CHO | 5 h | 70% |
| Example 64 | 10 | 5 | n-pentyl-CH(OCOPh)-CHO | 5 h | 75% |
| Example 65 | 10 | 5 | Ph(CH₂)₃-CH(OCOPh)-CHO | 4 h | 87% |
| Example 66 | 10 | 5 | EtO₂C(CH₂)₃-CH(OCOPh)-CHO | 4 h | 73% |
| Example 67 | 10 | 5 | BnO(CH₂)₄-CH(OCOPh)-CHO | 5 h | 70% |
| Example 68 | 10 | 5 | TBSO(CH₂)₅-CH(OCOPh)-CHO | 4 h | 81% |
| Example 69 | 10 | 5 | MOMO(CH₂)₅-CH(OCOPh)-CHO | 4 h | 77% |
| Example 70 | 10 | 5 | Cl(CH₂)₆-CH(OCOPh)-CHO | 4 h | 75% |
| Example 71 | 10 | 5 | CH₂=CH(CH₂)₈-CH(OCOPh)-CHO | 4 h | 78% |
| Example 72 | 10 | 5 | cis-CH₃(CH₂)₇CH=CH(CH₂)₇-CH(OCOPh)-CHO | 4 h | 77% |

The spectral data of the products obtained in Examples 62-72 are as follows.

The product obtained in Example 62: TLC, $R_f$=0.47 (hexane-EtOAc=1:1); IR (neat) 3032, 2925, 1726, 1408, 1269, 1187, 1073 cm$^{-1}$; $^1$H NMR (CDCl$_3$, 400 MHz) δ 3.09 (dd, J=8.4, 14.7 Hz, 1H), 3.22 (dd, J=4.5, 14.7 Hz, 1H), 5.29 (dd, J=4.5, 8.4 Hz, 1H), 5.92 (dd, J=0.9, 10.4 Hz, 1H), 6.18 (dd, J=10.4, 17.4 Hz, 1H), 6.46 (dd, J=1.4, 17.4 Hz, 1H), 7.20-7.34 (m, 5H), 9.58 (s, 1H); $^{13}$C NMR (CDCl$_3$, 100 MHz) δ 35.1, 78.7, 127.1, 127.2, 128.6, 129.3, 132.4, 135.3, 165.4, 198.0; HRMS (FAB+) m/z calcd for C$_{12}$H$_{13}$O$_3$ (M+H) 205.0865. found 205.0865.

The product obtained in Example 63: TLC, $R_f$=0.50 (hexane-EtOAc=1:1); IR (neat) 2927, 1740, 1719, 1455, 1295, 1163 cm$^{-1}$; $^1$H NMR (CDCl$_3$, 400 MHz) δ 1.95 (s, 3H), 3.09 (dd, J=8.6, 14.7 Hz, 1H), 3.21 (dd, J=4.8, 14.7 Hz, 1H), 5.23 (ddd, J=0.9, 4.8, 8.6 Hz, 1H), 5.65 (t, J=1.4 Hz, 1H), 6.18 (t, J=1.4, Hz, 1H), 7.20-7.34 (m, 5H), 9.58 (d, J=0.9 Hz, 1H); $^{13}$C NMR (CDCl$_3$, 100 MHz) δ 18.1, 35.2, 78.9, 127.1, 128.6, 129.4, 135.2, 135.4, 166.7, 198.3; HRMS (FAB+) m/z calcd for $C_{13}H_{15}O_3$ (M+H) 219.1021. found 219.1020.

The product obtained in Example 64: TLC, $R_f$=0.37 (hexane-EtOAc=4:1); IR (neat) 2960, 2930, 2861, 1722, 1452, 1273, 1112 cm$^{-1}$; $^1$H NMR (CDCl$_3$, 400 MHz) δ 0.90 (t, J=6.9 Hz, 3H), 1.26-1.42 (m, 4H), 1.46-1.57 (m, 2H), 1.78-2.01 (m, 2H), 5.22 (dd, J=5.1, 8.2 Hz, 1H), 7.46-7.51 (m, 2H), 7.59-7.64 (m, 1H), 8.08-8.12 (m, 2H), 9.64 (s, 1H); $^{13}$C NMR (CDCl$_3$, 100 MHz) δ 13.9, 22.3, 24.6, 28.7, 31.3, 78.7, 128.4, 129.1, 129.7, 133.4, 166.1, 198.5; HRMS (FAB+) m/z calcd for $C_{14}H_{19}O_3$ (M+H) 235.1334. found 235.1333.

The product obtained in Example 65: TLC, $R_f$=0.34 (hexane-EtOAc=4:1); IR (neat) 2935, 2860, 1740, 1720, 1452, 1272, 1114 cm$^{-1}$; $^1$H NMR (CDCl$_3$, 400 MHz) δ 1.51-1.60 (m, 2H), 1.66-1.76 (m, 2H), 1.87-2.04 (m, 2H), 2.64 (t, J=7.8 Hz, 2H), 5.21 (dd, J=5.0, 8.2 Hz, 1H), 7.15-7.20 (m, 3H), 7.24-7.30 (m, 2H), 7.45-7.51 (m, 2H), 7.59-7.64 (m, 1H), 8.06-8.10 (m, 2H), 9.63 (s, 1H); $^{13}$C NMR (CDCl$_3$, 100 MHz) δ 24.4, 28.6, 30.9, 35.4, 78.5, 125.7, 128.2, 128.3, 128.4, 129.0, 129.7, 133.4, 141.9, 166.0, 198.4; HRMS (FAB+) m/z calcd for $C_{19}H_{21}O_3$ (M+H) 297.1491. found 297.1496.

The product obtained in Example 66: TLC, $R_f$=0.47 (hexane-EtOAc=1:1); IR (neat) 2979, 1726, 1452, 1273, 1176, 1115 cm$^{-1}$; $^1$H NMR (CDCl$_3$, 400 MHz) δ 1.26 (t, J=6.9 Hz, 3H), 1.82-2.08 (m, 4H), 2.40 (t, J=7.3 Hz, 2H), 4.14 (q, J=6.9 Hz, 2H), 5.24 (dd, J=4.6, 8.7 Hz, 1H), 7.46-7.52 (m, 2H), 7.59-7.64 (m, 1H), 8.09-8.14 (m, 2H), 9.65 (s, 1H); $^{13}$C NMR (CDCl$_3$, 100 MHz) δ 14.1, 20.4, 28.2, 33.6, 60.4, 78.3, 128.5, 129.0, 129.8, 133.6, 166.0, 172.8, 198.1; HRMS (FAB+) m/z calcd for $C_{15}H_{19}O_5$ (M+H) 279.1232. found 279.1232.

The product obtained in Example 67: TLC, $R_f$=0.32 (hexane-EtOAc=1:1); IR (neat) 2934, 2863, 1720, 1453, 1272, 1113, 1027 cm$^{-1}$; $^1$H NMR (CDCl$_3$, 400 MHz) δ 1.57-1.75 (m, 4H), 1.86-2.04 (m, 2H), 3.49 (t, J=6.4 Hz, 2H), 4.49 (s, 2H), 5.22 (dd, J=4.4, 8.2 Hz, 1H), 7.23-7.36 (m, 5H), 7.44-7.50 (m, 2H), 7.58-7.63 (m, 1H), 8.08-8.12 (m, 2H), 9.62 (s, 1H); $^{13}$C NMR (CDCl$_3$, 100 MHz) δ 21.8, 28.6, 29.3, 69.6, 72.8, 78.6, 127.4, 127.5, 128.3, 128.4, 129.0, 129.8, 133.5, 138.3, 166.0, 198.3; HRMS (FAB+) m/z calcd for $C_{20}H_{23}O_4$ (M+H) 327.1596. found 327.1597.

The product obtained in Example 68: TLC, $R_f$=0.40 (hexane-EtOAc=4:1); IR (neat) 2930, 2857, 1740, 1723, 1269, 1098 cm$^{-1}$; $^1$H NMR (CDCl$_3$, 400 MHz) δ 0.04 (s, 6H), 0.88 (s, 9H), 1.33-1.45 (m, 4H), 1.48-1.56 (m, 4H), 1.85-2.00 (m, 2H), 3.60 (t, J=6.4 Hz, 2H), 5.22 (dd, J=4.6, 8.2 Hz, 1H), 7.46-7.51 (m, 2H), 7.59-7.64 (m, 1H), 8.08-8.12 (m, 2H), 9.64 (s, 1H); $^{13}$C NMR (CDCl$_3$, 100 MHz) δ −5.36, 18.3, 24.9, 25.5, 25.9, 28.7, 29.0, 32.6, 63.0, 78.7, 128.4, 129.1, 129.7, 133.4, 166.0, 198.4; HRMS (FAB+) m/z calcd for $C_{21}H_{35}O_4Si$ (M+H) 379.2305. found 379.2311.

The product obtained in Example 69: TLC, $R_f$=0.45 (hexane-EtOAc=1:1); IR (neat) 2934, 1721, 1452, 1271, 1112, 1044 cm$^{-1}$; $^1$H NMR (CDCl$_3$, 400 MHz) δ 1.30-1.45 (m, 4H), 1.45-1.70 (m, 4H), 1.86-2.02 (m, 2H), 3.35 (s, 3H), 3.52 (t, J=6.4 Hz, 2H), 4.61 (s, 2H), 5.22 (dd, J=5.0, 8.2 Hz, 1H), 7.46-7.52 (m, 2H), 7.59-7.64 (m, 1H), 8.09-8.12 (m, 2H), 9.64 (s, 1H); $^{13}$C NMR (CDCl$_3$, 100 MHz) δ 24.9, 25.9, 28.7, 29.0, 29.5, 55.0, 67.5, 78.6, 96.3, 128.4, 129.0, 129.7, 133.5, 166.0, 198.4; HRMS (FAB+) m/z calcd for $C_{17}H_{25}O_5$ (M+H) 309.1702. found 309.1711.

The product obtained in Example 70: TLC, $R_f$=0.56 (hexane-EtOAc=4:1); IR (neat) 2936, 1740, 1720, 1452, 1272, 1114 cm$^{-1}$; $^1$H NMR (CDCl$_3$, 400 MHz) δ 1.35-1.58 (m, 6H), 1.74-1.82 (m, 2H), 1.86-2.02 (m, 2H), 3.53 (t, J=6.9 Hz, 2H), 5.23 (dd, J=4.2, 8.2 Hz, 1H), 7.46-7.52 (m, 2H), 7.59-7.65 (m, 1H), 8.09-8.12 (m, 2H), 9.65 (s, 1H); $^{13}$C NMR (CDCl$_3$, 100 MHz) δ 24.8, 26.5, 28.5, 28.7, 32.3, 44.9, 78.6, 128.5, 129.0, 129.8, 133.5, 166.1, 198.5; HRMS (FAB+) m/z calcd for $C_{15}H_{20}ClO_3$ (M+H) 283.1101. found 283.1100.

The product obtained in Example 71: TLC, $R_f$=0.40 (hexane-EtOAc=4:1); IR (neat) 2927, 2855, 1740, 1722, 1452, 1271, 1113 cm$^{-1}$; $^1$H NMR (CDCl$_3$, 400 MHz) δ 1.25-1.41 (m, 8H), 1.47-1.55 (m, 2H), 1.85-1.98 (m, 2H), 2.00-2.07 (m, 2H), 4.89-5.02 (m, 2H), 5.22 (dd, J=4.6, 8.2 Hz, 1H), 5.80 (tdd, J=6.4, 10.1, 17.0 Hz, 1H), 7.46-7.52 (m, 2H), 7.59-7.64 (m, 1H), 8.09-8.13 (m, 2H), 9.64 (d, J=0.9 Hz, 1H); $^{13}$C NMR (CDCl$_3$, 100 MHz) δ 24.9, 28.7, 28.8, 28.9, 29.1, 29.2, 33.7, 78.7, 114.2, 128.5, 129.1, 129.8, 133.5, 139.0, 166.1, 198.6; HRMS (FAB+) m/z calcd for $C_{18}H_{25}O_3$ (M+H) 289.1804. found 289.1801.

The product obtained in Example 72: TLC, $R_f$=0.43 (hexane-EtOAc=4:1); IR (neat) 2925, 2854, 1740, 1724, 1453, 1270, 1112 cm$^{-1}$; $^1$H NMR (CDCl$_3$, 400 MHz) δ 0.88 (t, J=6.8 Hz, 3H), 1.18-1.43 (m, 18H), 1.46-1.56 (m, 2H), 1.85-2.07 (m, 6H), 5.22 (dd, J=5.0, 8.2 Hz, 1H), 5.29-5.39 (m, 2H), 7.46-7.52 (m, 2H), 7.59-7.64 (m, 1H), 8.09-8.12 (m, 2H), 9.64 (s, 1H); $^{13}$C NMR (CDCl$_3$, 100 MHz) δ 14.1, 22.6, 24.9, 27.0, 27.1, 28.8, 28.9, 29.1, 29.2, 29.4, 29.5, 29.6, 29.7, 31.8, 78.7, 128.4, 129.1, 129.5, 129.8, 130.0, 133.4, 166.0, 198.4; HRMS (FAB+) m/z calcd for $C_{25}H_{39}O_3$ (M+H) 387.2899. found 387.2900.

Examples 73 to 77

An intermolecular oxidative coupling reaction between propiophenone and benzoic acid was performed using TBHP (decane solution) as the oxidizer and ethyl acetate as the solvent, and the substrate concentration was examined. An experiment was conducted according to the procedures of Example 1. The results are shown in Table 8. The substrate concentration is shown by the number of moles of propiophenone per volume of ethyl acetate. Table 8 indicates that the reaction efficiently proceeded regardless of the substrate concentration (Examples 73 to 76). In addition, even when ethyl acetate was not used, the reaction efficiently proceeded (Example 77).

TABLE 8

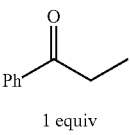

| | Oxidizer | Substrate concentration | Yield (%) |
|---|---|---|---|
| Example 73 | 5.5 M TBHP decane solution | 0.1 M | 59 |
| Example 74 | 5.5 M TBHP decane solution | 0.2 M | 77 |
| Example 75 | 5.5 M TBHP decane solution | 0.4 M | 80 |
| Example 76 | 5.5 M TBHP decane solution | 0.6 M | 76 |
| Example 77 | 5.5 M TBHP decane solution | — | 64 |

Examples 78 to 82

An intermolecular oxidative coupling reaction between a carbonyl compound and a carboxylic acid was variously examined. That is, ketone $R^1C(=O)CH_2R^2$ and carboxylic acid (methacrylic acid or benzoic acid) were used so as to produce products shown in Table 9, and the reaction was performed according to Example 1 under reaction conditions shown in Table 9. The results are shown in Table 9.

TABLE 9

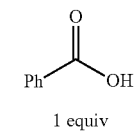

| | Product | Bu$_4$NI (mol %) | Piperidine (mol %) | conditions | Yield (%) |
|---|---|---|---|---|---|
| Example 78 | 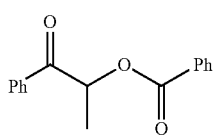 [SMILES: CC(OC(=O)c1ccccc1)C(=O)c1ccccc1] | 10 | 10 | 75° C., 24 h | 13 |
| Example 79 | 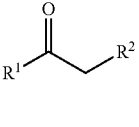 | 10 | — | 75° C., 6 h | 13 |

TABLE 9-continued

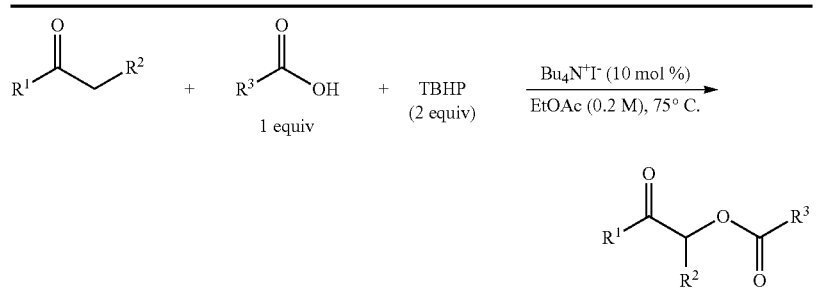

| | Product | Bu4NI (mol %) | Piperidine (mol %) | conditions | Yield (%) |
|---|---|---|---|---|---|
| Example 80 | | 10 | — | 75° C., 24 h | 22 |
| Example 81 | | 10 | — | 75° C., 32 h | 22 |
| Exampl 82 | | 5 | — | 50° C., 6 h | 69 |

The spectral data of the products described in Table 9 are as follows.

The product obtained in Example 78: $^1$H NMR (CDCl$_3$, 300 MHz) δ 1.98 (s, 3H), 2.53-2.59 (m, 1H), 2.75-2.83 (m, 1H), 3.60-3.73 (m, 2H), 4.26-4.32 (m, 1H), 4.33-4.40 (m, 1H), 5.28 (dd, J=7.1, 10.6 Hz, 1H), 5.67 (s, 1H), 6.20 (s, 1H).

The product obtained in Example 79: TLC, R$_f$=0.33 (hexane-EtOAc=4:1); $^1$H NMR (CDCl$_3$, 300 MHz) δ 1.99 (s, 3H), 3.10 (dd, J=4.8, 17.4 Hz, 1H), 3.67 (dd, J=7.0, 17.4 Hz, 1H), 5.43 (dd, J=4.8, 8.0 Hz, 1H), 5.67 (s, 1H), 6.22 (s, 1H), 7.55-7.60 (m, 1H), 7.64-7.70 (m, 2H).

The product obtained in Example 80: R$_f$=0.30 (hexane-EtOAc=4:1); $^1$H NMR (CDCl$_3$, 300 MHz) δ 2.03 (s, 3H), 2.29-2.41 (m, 1H), 2.41-2.49 (m, 1H), 3.07-3.15 (m, 1H), 3.19-3.30 (m, 1H), 5.62 (dd, J=5.0, 13.2 Hz, 1H), 5.67 (s, 1H), 6.26 (s, 1H), 7.25-7.31 (m, 1H), 7.31-7.37 (m, 1H), 7.49-7.55 (m, 1H), 8.01-8.06 (m, 1H).

The product obtained in Example 81: R$_f$=0.32 (hexane-EtOAc=4:1); $^1$H NMR (CDCl$_3$, 300 MHz) δ 2.38-2.51 (m, 1H), 2.51-2.59 (m, 1H), 3.11-3.20 (m, 1H), 3.26-3.35 (m, 1H), 5.81 (dd, J=5.0, 13.3 Hz, 1H), 7.28-7.33 (m, 1H), 7.33-7.39 (m, 1H), 7.44-7.50 (m, 2H), 7.50-7.57 (m, 1H), 7.57-7.62 (m, 1H), 8.06 (dd, J=0.9, 7.8 Hz, 1H), 8.13-8.18 (m, 2H).

The product obtained in Example 82: TLC, R$_f$=0.45 (hexane-EtOAc=4:1); $^1$H NMR (CDCl$_3$, 400 MHz) δ 2.00 (s, 3H), 5.67 (s, 1H), 6.22 (s, 1H), 6.90 (s, 1H), 7.33-7.45 (m, 5H), 7.46-7.56 (m, 3H), 7.93-7.99 (m, 2H); NMR (CDCl$_3$, 100 MHz) δ 18.2, 77.6, 126.9, 128.5, 128.6, 128.7, 129.0, 129.2, 133.4, 133.6, 134.6, 135.4, 166.7, 193.8.

Examples 83 to 87

An intermolecular oxidative coupling reaction between 4-tert-butylcyclohexanone and methacrylic acid was variously examined. That is, the reaction was performed according to Example 1 under reaction conditions shown in Table 10. The results are shown in Table 10. This reaction produced unidentified by-products in addition to monoacyloxy and diacyloxy compounds. Both the monoacyloxy and diacyloxy compounds were single diastereomers (all substituents were equatorial).

TABLE 10

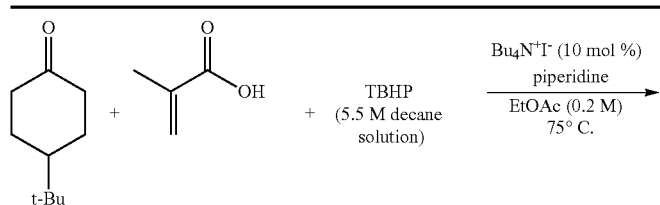

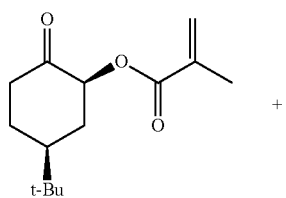

Monoacyloxy compound

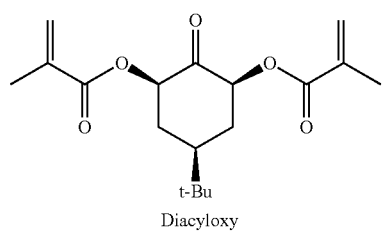

Diacyloxy compound

|  | Additive | Reaction time | Yield[*1] | Mono-Di |
|---|---|---|---|---|
| Example 83 | — | 24 h | ca. 35% | ca. 25:10 |
| Example 84 | piperidine 5 mol % | 19 h | ca. 40% | ca. 30:10 |
| Example 85 | piperidine 10 mol % | 24 h | ca. 45% | ca. 35:10 |
| Example 86 | morpholine 10 mol % | 19 h | ca. 40% | ca. 30:10 |
| Example 87 | n-hexylamine 10 mol % | 24 h | ca. 40% | ca. 35:5 |

[*1] Yield was obtained by NMR analysis of reaction mixture after completion of reaction, from which removed unidentified products.

The spectral data of the products obtained in Examples 83-87 are as follows.

Monoacyloxy compound: $R_f$=0.26 (hexane-EtOAc=8:1); $^1$H NMR (CDCl$_3$, 300 MHz) δ 0.95 (s, 9H), 1.39-1.52 (m, 1H), 1.58-1.78 (m, 2H), 1.98 (s, 3H), 2.08-2.17 (m, 1H), 2.32-2.39 (m, 1H), 2.44 (ddd, J=0.9, 6.0, 14.0 Hz, 1H), 2.52 (ddd, J=2.7, 4.6, 14.0 Hz, 1H), 5.28 (dd, J=6.4, 12.4 Hz, 1H), 5.63 (s, 1H), 6.21 (s, 1H); $^{13}$C NMR (CDCl$_3$, 100 MHz) δ 18.3, 27.6, 28.0, 32.4, 34.1, 39.5, 45.8, 76.2, 126.2, 135.7, 166.3, 204.8.

Diacyloxy compound: $R_f$=0.24 (hexane-EtOAc=8:1); $^1$H NMR (CDCl$_3$, 300 MHz) δ 0.98 (s, 9H), 1.61-1.71 (m, 2H), 1.78-1.89 (m, 1H), 1.97 (s, 6H), 2.35-2.44 (m, 2H), 5.39 (dd, J=6.0, 12.8 Hz, 2H), 5.63 (s, 2H), 6.22 (s, 2H); $^{13}$C NMR (CDCl$_3$, 100 MHz) d 18.2, 27.5, 32.4, 33.9, 41.5, 74.8, 166.0, 198.9.

Examples 88 to 90

The type of an oxidizer used in an intermolecular oxidative coupling reaction was examined. The results are shown in Table 11. In Examples 88 and 89, the reaction between propiophenone and methacrylic acid was performed using as an oxidizer a water solution of hydrogen peroxide and cumene hydroperoxide, respectively. In Table 11, "%" of the oxidizer is "% by mass". For reference, Table 11 also shows the results of Example 49 using TBHP as the oxidizer in the same reaction. With any one of the oxidizers, the target compound, α-acyloxycarbonyl compound, was produced apart from the yield. In Example 90, a reaction between propiophenone and benzoic acid was performed using cumene hydroperoxide as the oxidizer. For reference, Table 11 also shows the results of Example 74 using TBHP as the oxidizer in the same reaction. With any one of the oxidizers, the target compound, α-acyloxycarbonyl compound, was produced.

TABLE 11

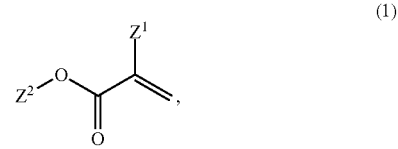

| | RCOOH | Oxidizer | Yield (%) |
|---|---|---|---|
| Example 88 | | 30% hydrogen peroxide solution | 5 |
| Example 89 | | 80% cumene hyddroperoxide solution | 46 |
| Example 49 | | 5.5 M TBHP decane solution | 61 |
| Example 90 | PhCOOH | 80% cumene hyddroperoxide solution | 65 |
| Example 74 | | 5.5 M TBHP decane solution | 77 |

This application claims the benefit of Japanese Patent Application No. 2010-049003 filed on Mar. 5, 2010, which is hereby incorporated by reference herein in its entirety.

INDUSTRIAL APPLICABILITY

The present invention can be mainly applied to the medicinal chemical industry. In particular, polymers produced by polymerizing α-acryloxyketone or α-methacryloxyketone prepared in Examples 25 to 28 can be used as antifouling paint compositions (refer to, for example, Japanese Unexamined Patent Application Publication No. 2009-144071) and positive resist materials (refer to, for example, Japanese Unexamined Patent Application Publication No. 2009-169406). In addition, Salvinorin A which attracts attention as a lead compound for curing central nervous system diseases such as psychosis, Alzheimer's disease, and the like has an α-acetoxyketone skeleton and thus a final product can be produced through shorter steps than usual by applying the production method of the present invention.

The invention claimed is:

1. A method for producing an α-acyloxycarbonyl compound by an intermolecular reaction, the method comprising: reacting a carboxylic acid and a carbonyl compound selected from the group consisting of a ketone, an aldehyde, and an ester, which comprise a hydrogen atom at the α-position, with an oxidizer, which is a hydroperoxide and a catalyst precursor, which is an iodide salt thereby introducing an acyloxy group derived from the carboxylic acid into the α-position of the carbonyl compound.

2. The method of claim 1, wherein the hydroperoxide is an organic hydroperoxide.

3. The method of claim 1, wherein the hydroperoxide is employed at 1 to 5 equivalents relative to, of the carboxylic acid and the carbonyl compound, one having a smaller number of moles.

4. The method of claim 1, wherein the iodide salt is at least one selected from the group consisting of an ammonium iodide, a phosphonium iodide, and an alkali metal iodide.

5. The method of claim 1, wherein the iodide salt is employed at 1 to 50 mol % relative to, of the carboxylic acid and the carbonyl compound, one having a smaller number of moles.

6. The method of claim 1, wherein at least one selected from the group consisting of an ether solvent, an ester solvent, and a nitrile solvent is employed as a reaction solvent.

7. The method of claim 1, wherein the reaction is performed at 25° C. or more.

8. The method of claim 1, wherein the carbonyl compound comprises a partial structure of —C(=O)—CH$_2$—.

9. The method of claim 1, wherein the reaction is performed in the presence of an amine.

10. The method of claim 1, wherein the carboxylic acid is an unsaturated aliphatic carboxylic acid.

11. An α-acyloxycarbonyl compound of formula (1):

$$\underset{Z^2-O}{\overset{Z^1}{\underset{O}{\parallel}}}$$ (1)

wherein:

$Z^1$ is H or CH$_3$;

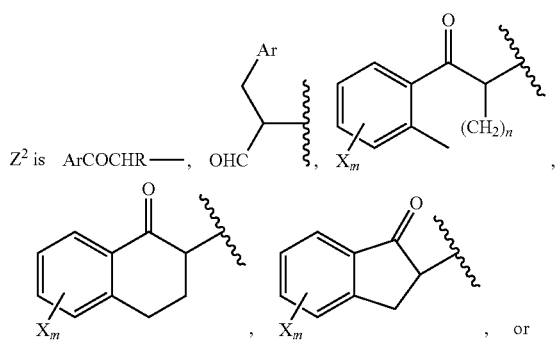

$Z^2$ is ArCOCHR—, OHC—, [structures], or

-continued

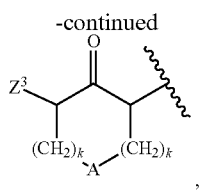

wherein:
Ar is a phenyl group, a phenyl group comprising an alkyl group, or a phenyl group comprising a halogen atom;
R is an alkyl group;
X is an alkyl group or a halogen atom;
m is an integer of 0 to 4;
n is an integer of 1 to 4;
k and k' are each an integer of 0 to 4 and k+k' is an integer of 1 to 4; and
A is O, S, NH, NR, or CHR, wherein R is an alkyl group; and
$Z^3$ is H or $CH_2=C(Z^1)COO-$.

12. The method of claim 2, wherein the organic hydroperoxide tert-butyl hydroperoxide and cumene hydroperoxide.

13. The method of claim 12, wherein the organic hydroperoxide is cumene hydroperoxide.

14. The method of claim 12, wherein the organic hydroperoxide is tert-butyl hydroperoxide.

15. The method of claim 12, wherein the hydroperoxide is employed at 1 to 5 equivalents relative to, of the carboxylic acid and the carbonyl compound, one having a smaller number of moles.

16. The method of claim 12, wherein the hydroperoxide is employed at 1.1 to 2.5 equivalents relative to, of the carboxylic acid and the carbonyl compound, one having a smaller number of moles.

17. The method of claim 1, wherein the iodide salt is employed at 5 to 20 mol % relative to, of the carboxylic acid and the carbonyl compound, one having a smaller number of moles.

18. The method of claim 16, wherein the iodide salt is employed at 5 to 20 mol % relative to, of the carboxylic acid and the carbonyl compound, one having a smaller number of moles.

19. The method of claim 1, wherein the reaction is performed at 50° C. or more.

20. The method of claim 1, wherein the reaction is performed at 50° C. or more and 100° C. or less.

\* \* \* \* \*